United States Patent [19]

Markandey

[11] Patent Number: 5,168,161
[45] Date of Patent: Dec. 1, 1992

[54] SYSTEM AND METHOD OF DETERMINING SURFACE CHARACTERISTICS USING INFRARED IMAGING

[75] Inventor: Vishal Markandey, Dallas, Tex.

[73] Assignee: Texas Instruments Incorporated, Dallas, Tex.

[21] Appl. No.: 510,631

[22] Filed: Apr. 18, 1990

[51] Int. Cl.$^5$ .......................................... G01N 25/18
[52] U.S. Cl. .................................... 250/330; 374/44
[58] Field of Search .......................... 374/44; 250/330

[56] References Cited

U.S. PATENT DOCUMENTS 3,868,508  2/1975  Lloyd ................................. 250/330
4,853,538  8/1989  Jackson .......................... 250/336.2

OTHER PUBLICATIONS

"Prediction of Temporal Changes of Natural Terrain Infrared Images", N. Ben-Yosef, K. Wilner, S. Lashansky, & M. Abitbol; SPIE, vol. 807 Passive Infrared Systems & Technology, 1987, pp. 58–60.

Ben-Yosef et al. "Natural terrain infrared radiance statistics: daily variation." *Applied Optics*, 24(23):4167–4171, 1985.

S. Geman and D. Geman, "Stochastic Relaxation, Gibbs Distribution, and the Bayesian Restoration of Images," *IEEE Transactions on Pattern Analysis and Machine Intelligence*, 6(6):721–741, Nov. 1984.

F. P. Incropera and D. P. DeWitt, Introduction to Heat Transfer. John Wiley & Sons, 1985 pp. 244–279.

C. Koch and et al. "Computing optical flow in resistive networks and in the primate visual system," In Proceedings: Workshop on Visual Motion, pp. 62–72, Mar. 1989.

J. Marroquin, S. Mitter, and T. Poggio, "Probabilistic Solution of Ill-Posed Problems in Computational Vision." Technical Report AI Memo 897, MIT, AI Lab, Mar. 1987.

N. Nandhakumar and J. K. Aggarwal, "Integrated analysis of thermal and visual images for scene interpretation." *IEEE Transactions on Pattern Analysis and Machine Intelligence*, 10(4):469–481, 1988.

Primary Examiner—Constantine Hannaher
Attorney, Agent, or Firm—Richard L. Donaldson; William E. Hiller; L. Joy Griebenow

[57] ABSTRACT

There is disclosed a system and method for generating characteristics of a surface using an analysis of the infrared image of the surface. A heat balance equation is generated and a technique is presented for solving the equation to generate the absorptivity and conductivity indices of the surface. These indices are matched against a data base of indices of various surfaces to achieve material identification. An embodiment is disclosed in which the indices are used to predict surface appearance in the infrared image for different points in time.

24 Claims, 1 Drawing Sheet

SYSTEM AND METHOD OF DETERMINING SURFACE CHARACTERISTICS USING INFRARED IMAGING

TECHNICAL FIELD OF THE INVENTION

This invention relates to imaging systems and more particularly to a system and method for identifying certain characteristics of a surface from its infrared image.

BACKGROUND OF THE INVENTION

It is now a common practice to identify surfaces, such as buildings, beaches, streets, etc., using various imaging techniques. These techniques, in essence, rely upon a prestored image or a data model, against which newly arriving image data is compared.

Techniques that use prestored images rely upon two basic givens, namely 1) that there is in fact the ability to create the pre-stored image in the first instance and 2) that a received image can be properly matched to the stored image.

In situations when a data model of objects is created, the following assumptions are made: 1) that an accurate model can be created and 2) that there are enough clues, or indices, in the stored data model and in the unknown image data to make a highly probable guess as to the identity of objects or surfaces in the image. Since dire results might occur if mistakes are made, particularly where such image comparisons are used for ordinance guidance, it is critically important that both of the above assumptions be true and that the pre-stored data be as accurate as possible.

In some situations, it is difficult at best to even generate the pre-stored image to the degree necessary for accurate error free subsequent image identification. One of these situations occurs when the image is subject to change over the course of time. A day and night infrared image of the same surface area would appear different because of the inherent difference in radiation conditions. Thus, when a factory is being imaged, that factory would have a different appearance in the infrared image depending upon the time of day and upon the ambient environmental conditions at the factory site. There are many other examples of images which have different characteristics at different points of time and it is not possible or feasible to obtain actual images of the same topography under all possible situations.

Thus, a need exists in the art for a system and method of generating pre-stored images representative of surfaces as they would appear under conditions other than when the image was actually generated.

A further need exists in the art for a system and method which can extract various indices from an image pertaining to the character of the surface, thereby increasing the probability of an accurate object identification from the image.

SUMMARY OF THE INVENTION

I have taken advantage of the fact that the absorptivity and conductivity values of a surface are unique to that surface and can be used to provide indices for subsequent identification of the surface. I have also used these factors to devise a system and method of computing synthetic images from a given image where the synthetic image represents the same image at a later period of time as the environmental conditions change.

It is thus a technical advantage of my invention to provide a method and system for taking advantage of the heat balance equation of a surface by solving that heat balance equation to derive certain indices of the objects or surface in the image. Using these indices, then, a system of surface identification can be constructed.

It is a further technical advantage of my invention that the absorptivity and conductivity indices of a surface derived from an actual image can be used to generate a synthetic image of the surface at a different point in time.

It is a still further technical advantage to provide a method of generating indices of a surface for storage in a data base by generating from a single image of a surface a heat balance equation of the surface and by solving the equation to obtain the heat absorptivity and conductivity of said surface to establish said indices.

It is a still further technical advantage to provide a system for identifying physical objects from infrared images of the objects by the system having circuitry for deriving a heat balance equation of the objects; and having circuitry for generating indices of the objects pertaining to the infrared absorptivity and conductivity of the objects from said derived heat balance equation; and having circuitry for comparing the generated indices with prestored indices.

A system for identifying physical objects from infrared images of the objects of the present invention comprises circuitry for deriving a heat balance equation of the objects, circuitry for generating indices of the objects pertaining to the infrared absorptivity and conductivity of the objects from the derived heat balance equation, and circuitry for comparing the generated indices with prestored indices. Alternatively, a method of identifying physical objects from infrared images of the objects of the present invention comprises the steps of deriving a heat balance equation of the objects, generating indices of the objects pertaining to the infrared absorptivity and conductivity of the objects from the derived heat balance equation, and comparing the generated indices with prestored indices.

BRIEF DESCRIPTION OF THE DRAWINGS

The foregoing problems, solutions and technical advantages are shown in more detail with reference to the drawings in which.

DETAILED DESCRIPTION OF THE INVENTION

First, we must derive a relationship between the various thermal radiation components and temperature distributions present at any surface in an outdoor scene. Consider the surface patch 10 shown in FIG. 1. $I_{inc}$ is the incident solar radiation. At the surface, this radiation is subject to three effects: absorption, reflection, and transmission. Most objects occurring in outdoor scenes are opaque to infrared (IR) radiation and so the transmission effect is negligible. The body also emits radiation of its own. According to the Stefan-Boltzmann law, the radiated power is proportional to the fourth power of the body's absolute temperature and to its emissivity. The sensor receives the emitted and reflected components of the radiation. The reflected component is negligible compared to the emitted component for two reasons. First, infrared radiation reflectivity values are low for most materials occurring in natural scenes such as vegetation, sand, soil, rocks, and painted metal and second because the sun's surface temperature is approximately 5672K, and according to Planck's law very little of its emitted radiation lies in the commonly used infrared wavelengths (8 to 12 $\mu$m), whereas objects in natural scenes with average temperatures of 250 to 350K emit primarily at these wavelengths.

Figure 1:
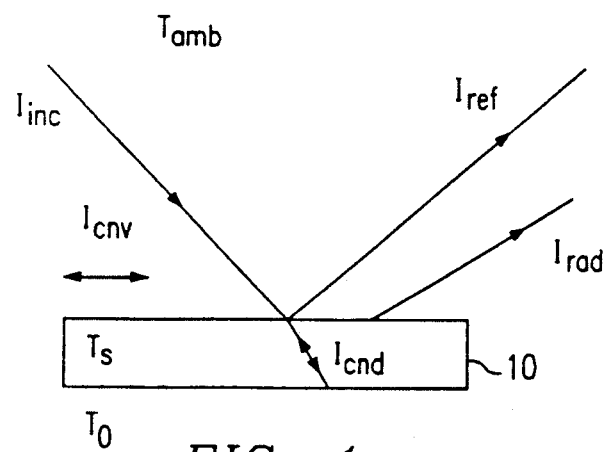
FIG. 1 shows the heat balance conditions at a surface.

In FIG. 1, the surface temperature of the body is represented as $T_s$, its interior temperature as $T_o$, $T_{amb}$ is the ambient temperature of the atmosphere, $I_{cnv}$ is the heat convected from the surface to the air, $I_{rad}$ is the emitted radiation, $I_{cnd}$ is the heat conducted from the object surface to its interior, and $I_{abs}$ is the total heat absorbed by the surface. At any point in time, a balance exists among the radiation components flowing into the object surface and those flowing out. This can be written as $$I_{abs} = I_{cnv} + I_{rad} + I_{cnd} \tag{1}$$

The various radiation components can be computed from the following relations:

$$I_{abs} = \eta f(t) \tag{2}$$

where $\eta$ is the absorptivity of the surface material and f(t) is the time dependent solar radiation incident on the object surface.

$$I_{cnv} = h(T_s - T_{amb}) \tag{3}$$

where h is the average convection heat transfer coefficient, and depends on the properties of the surrounding air (e.g., air velocity, viscosity, temperature etc.), and also to some extent on the geometry of the surface. The effect of the surface geometry can be ignored for typical wind velocities up to 15 mph as the convection tends to be laminar and convection relations developed for external flow over flat plates can be used. For higher wind velocities the convection becomes turbulent and object geometry will have an appreciable effect on it. For the present we ignore such situations. Numerous empirical techniques exist for computing h and some of them are given by F. P. Incropera and D. P. DeWitt in their book "*Introduction to Heat Transfer*" published by John Wiley & Sons, 1985.

$$I_{rad} = \sigma \epsilon (T_s^4 - T_{amb}^4) \tag{4}$$

where $\sigma$ is the Stefan-Boltzmann constant ($5.670 \times 10^{-8}$ W/m.K$^4$), $\epsilon$ is the emissivity of the object. Most objects in natural scenes have emissivity values close to 0.9, so a constant value of 0.9 is assumed for all bodies.

$$I_{cnd} = \xi (T_s - T_o) \tag{5}$$

where $\xi$ is the element conductivity. Note that the values of $\eta$ and $\xi$ vary from surface to surface and are indicative of the surface material. In terms of these relations (2)–(5), equation (1) above can be rewritten as:

$$\eta f(t) = h(T_s - T_{amb}) + \sigma \epsilon (T_s^4 - T_{amb}^4) + \xi (T_s - T_o) \tag{6}$$

The above equation is the heat balance equation. This equation is valid on a pixel to pixel basis for a given infrared image. In this equation f(t) is assumed known, $T_{amb}$ can be measured, and while $T_o$ need not be constant for the entire region being imaged, it is assumed so as a first approximation. The computation of h has already been discussed above, and we use the following method to compute $T_s$ from the grey-scale infrared image. This method is given in detail by N. Nandhakumar and J. K. Aggarwal in their paper entitled "Integrated Analysis of Thermal and Visual Images for Scene Interpretation" published in *IEEE Transactions on Pattern Analysis and Machine Intelligence*, corresponding to a surface temperature $T_s$ then $$K_a G_i + K_b = \int_{\lambda_1}^{\lambda_2} \frac{\epsilon C_1 \tau_{\lambda R}}{\lambda^5 (\exp(C_2/\lambda T_s) - 1)} d\lambda \tag{7}$$

In this equation $K_a$ and $K_b$ are calibration constants of the imaging system. The quantity on the right hand side corresponds to radiation in the infrared band received by the sensor. ($\lambda_1$, $\lambda_2$) is the range of infrared wave lengths being imaged. Typically $\lambda_1 = 8$ $\mu$m ad $\lambda_2 = 12$ $\mu$m. $C_1$ and $C_2$ are universal constants. $C_1 = 3.742 \times 10^8$ W.$\mu$m/m$_2$ and $C_2 = 1.439 \times 10^4$ $\mu$m K. $\epsilon$ is the surface emissivity, assumed 0.9 as explained previously. $T_{\lambda R}$ is the spectral atmospheric transmission for range R, obtained from the standard LOWTRAN codes. $K_a$ and $K_b$ are obtained by imaging two bodies at different known temperatures. The corresponding grey scale values are measured and substituted along with $T_s$ in the above equation to obtain two linear equations in the unknowns $K_a$ and $K_b$ which can then be solved for these parameters. It is then desired to compute $T_s$ for any given $G_i$. Current techniques do this by precomputing the integral in the above equation for various values of $T_s$ and creating a table of these values. The observed grey scale is used to compute the left side of the above equation and this value is then matched to the table to get the corresponding $T_s$.

The unknowns in the heat balance equation are $\eta$ and $\xi$. These values will change from pixel to pixel and because of the continuity of the physical surfaces being imaged, the values at any given pixel will be related to those at the neighboring pixels. This equation has to be solved for $\eta$ and $\xi$ on a pixel to pixel basis. This is a linear equation in the unknowns, and as there are two unknowns but only one equation, it is an ill-posed problem. Solution methodologies for ill-posed problems are an extensive field in mathematics, and many well-known techniques exist.

One powerful technique is Bayesian estimation using Markov random fields (MRFs). MRFs have been used by various researchers in computer vision and image processing, such as by S. Geman and D. Geman; reported in "Stochastic Relaxation, Gibbs Distribution, and the Bayesian Restoration of Images," published by *IEEE Transactions on Pattern Analysis and Machine Intelligence*, 6(6):721-741, Nov. 1984 and as by J. Marroquin, S. Mitter, and T. Poggio reported in "*Probabilistic Solution of Ill-Posed Problems in Computational Vi-* sion," Technical Report AI Memo 897, published by MIT, AI Lab, Mar. 1987.

The following discussion of MRFs derives from the above-identified work. MRFs are particularly amenable to scene modeling as they incorporate the spatial dependence of pixels in relative proximity to each other. To solve the ill-posed problem, a probability density is used to represent the a priori knowledge of the relationship between neighboring pixels. This probability distribution, along with a noise description, distribution, can be used to compute the posteriori probability distribution P(f/g) which represents the probability of the solution f for an observation g. The idea is to find f which maximizes this probability for the given observation. This is called the Maximum A Priori (MAP) estimate. By the Clifford-Hammersley theorem, the prior probability has the Gibbs form:

$$P(f) \frac{1}{Z} e^{\frac{-u(f)}{T}} \quad (8)$$

where Z and T are constants and $U(f) = \Sigma_c U_c(f)$ is an energy function that can be computed as the sum of local contributions from each neighborhood. When the surfaces are smooth we have:

$$U_c(f) = (f_i - f_j)^2 \quad (9)$$

where i is the pixel under consideration and j is one of its neighbors from a suitably defined neighborhood. Knowing the noise model and invoking Bayes theorem, we can then find the probability distribution P(f/g) and find the $\eta$ and $\xi$ distributions using Monte Carlo techniques such as the Metropolis algorithm.

Such techniques are very powerful, but also computationally intensive. However, they are also very amenable to parallel implementation. J. Marroquin, S. Mitter, and T. Poggio discuss parallelisation schemes for implementing such techniques in their paper *"Probabilistic Solution of Ill-Posed Problems in Computational Vision,"* Technical Report AI Memo 897, published by MIT, AI Lab, Mar. 1987. As far as our current efforts are concerned, rather than unleashing the full power of Bayesian estimation using MRFs we have considered the much simpler and computationally cheaper approach suggested by Tikhonov's regularization methodology. Of course this simple methodology has its limitations, primary among them being its inability to deal with discontinuities in solution space, such as discontinuities in thermal parameter values that will arise at the boundaries between target and terrain. To overcome this problem we will have to take recourse to MRFs at a later stage. The MRF based approach outlined above can be extended to take care of such situations by modifying $U_c(f)$ to incorporate line processes. The use of line processes with MRF models was suggested by S. Geman and D. Geman in their above-identified paper, and they have been recently used by C. Koch et al to compute optical flow in the presence of motion boundaries as reported in their paper "Computing Optical Flow in Resistive Networks and in the Primate Visual System," published in *Proceedings: Workshop on Visual Motion*, pages 62-72, Mar. 1989. For now we ignore these issues and use the regularization approach, principally because of its computational simplicity. It may be noted that regularization methods may be considered a special case of the MRF model approach in the following sense as suggested by J. Marroquin, S. Mitter, and T. Poggio in their above-mentioned paper. The MAP estimate leads to a minimization of a quadratic functional of the regularization type, when the MRF is continuous-valued, the noise is Gaussian and additive, and first order differences are zero-mean, independent, Gaussian random variables. Using the regularization approach we estimate the $\eta$ and $\xi$ values from the heat balance equation by imposing a "smoothness constraint" which penalizes abrupt changes in the values of these parameters from pixel to neighboring pixel. Physically this corresponds to the fact that the physical parameters will not change drastically from point to adjacent point on an object. The heat balance equation can be restated as $$\eta A = \xi B + C \quad (10)$$

This equation is valid on a pixel-to-pixel basis, and $\eta$, $\xi$, B, and C are functions of (x,y) where (x,y) is the pixel coordinate system and A is f(t). Using the standard approach of regularization we define the stabilizing functional $$e_s = \int\int (\xi_x^2 + \xi_y^2 + \eta_x^2 \eta_y^2) dx dy \quad (11)$$

and use the quadratic norm $$e_c = \int\int (\eta A - \xi B - C)^2 dx dy \quad (12)$$

Defining $\lambda$ as the regularization parameter, we have to find the solution that minimizes $$e = e_s + \lambda e_c \quad (13)$$

Calculus of variations can be used to solve this problem. The Euler equations yield a coupled pair of elliptic second-order partial differential equations that can be solved by iterative methods. The final iterative solution for a discretized version of the problem is given below $$\eta_{kl}^{n+1} = \frac{\eta_{kl}^n (1 + \lambda \overline{B_{kl}^2}) + \xi_{kl}^n (\lambda \overline{A_t B_{kl}}) + \lambda C_{kl} A_t}{1 + \lambda (\overline{A_t^2} + \overline{B_{kl}^2})} \quad (14)$$

$$\xi_{kl}^{n+1} = \frac{\eta_{kl}^n (\lambda \overline{A_t B_{kl}}) + \xi_{kl}^n (1 + \lambda \overline{A_t^2}) - \lambda C_{kl} B_{kl}}{1 + \lambda (\overline{A_{kl}^2} + \overline{B_{kl}^2})} \quad (15)$$

In the above relations n is the number of iterations, (k,l) is the pixel location, and the quantities under bars are the average values for pixel neighborhoods centered at (k,l); t is the time parameter to show that A is a time dependent quantity.

Figure 2:
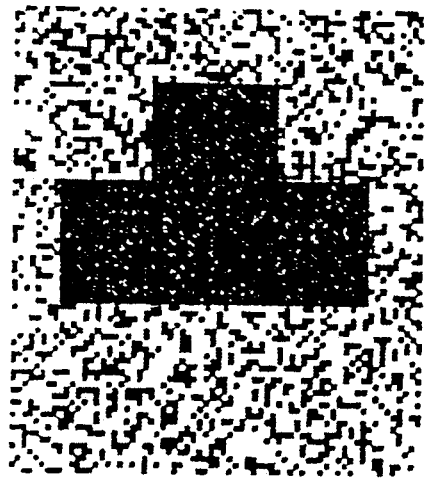
FIGS. 2 and 3 show synthetic inputs to illustrate the principles of the invention.
Figure 3:
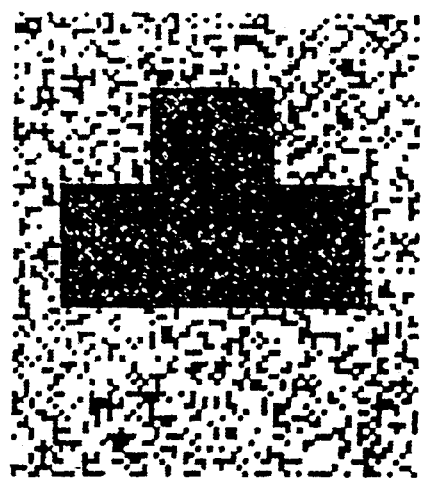
Figure 4:
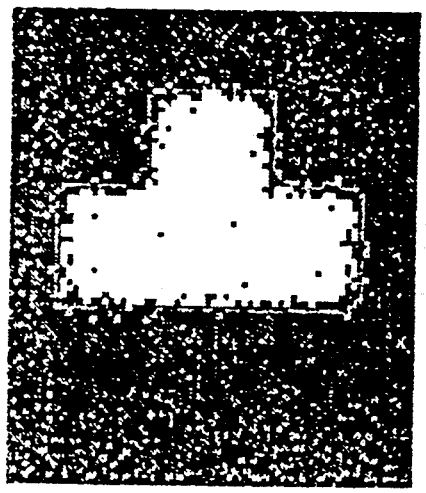
FIG. 4 shows the absorptivity values computed by the inventive method and system.
Figure 5:
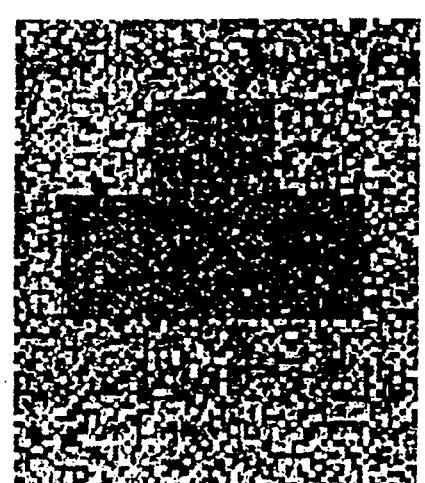
FIG. 5 shows the conductivity values computed by the inventive method and system.

To illustrate the technique for estimating absorptivity and conductivity values from forward looking infrared (FLIR) images, consider the simplified example illustrated in FIGS. 2 through 5. I have made the following simplifications in this example: I consider equation (10) to be the starting point. It is assumed that the values of A, B, and C parameters are given as two-dimensional arrays, and the corresponding values of $\eta$ (absorptivity) and $\xi$ (conductivity) are to be computed. Note that no effort has been made in this example to relate the values of A, B, and C to the physical parameters in the heat balance equation (equation (6)). As such, the example is completely synthetic and the values computed for $\eta$ and $\xi$ do not correspond to physically meaningful quantities. They are simply a solution of the linear equation represented by equation (10). In the example, the parameter A, which is actually f(t) in the heat balance equation, is not a function of (x,y) and is set to a constant value. FIGS. 2 and 3 show the B and C arrays respectively. This is the input for the example. FIGS. 4 and 5 show the solutions obtained for the $\eta$ and $\xi$ values respectively.

A method of generating indices of a surface for storage in a data base of the present invention comprises the steps of generating from single image of a surface a heat balance equation of the surface and solving the equation from the single image to obtain the heat absorptivity and conductivity of the surface to establish the indices. Such method may further comprise the steps of obtaining a single new image of a surface, generating a heat balance equation of the single new image, solving the new image equation to obtain heat absorptivity and conductivity of the new image to establish indices of said new image, comparing the new image indices to indices stored in the data base; and generating a probable match between previous stored surface indices and the indices of the new image. Such method may be used wherein the indices for a given surface area are broken into regions and further include the step of comparing individual index regions of a new surface against similar individual stored index regions. Additionally, such method may be used wherein the index regions contain curves and corners and further include the steps of detecting the curves and corners of the index regions computed from the new image, and matching the detected curves and corners against curves and corners of the stored index regions.

Alternatively, a circuit for generating indices of a surface for storage in a data base of the present invention comprises circuitry for generating from single image of a surface a heat balance equation of the surface and circuitry for solving the equation from the single image to obtain the heat absorptivity and conductivity of the surface to establish the indices. Such circuit may further comprise circuitry for obtaining a single new image of a surface, circuitry for generating a heat balance equation of the single new image, circuitry for solving the new image equation to obtain heat absorptivity and conductivity of the new image to establish indices of said new image, circuitry for comparing the new image indices to indices stored in the data base and circuitry for generating a probable match between previous stored surface indices and the indices of the new image. Such circuit may be used wherein the indices for a given surface area are broken into regions and further include circuitry for comparing individual index regions of a new surface against similar individual stored index regions. Additionally, such circuit may be used wherein the index regions contain curves and corners and further include circuitry for detecting the curves and corners of the index regions computed from the new image, and circuitry for matching the detected curves and corners against curves and corners of the stored index regions.

An approach to object classification can be devised by matching material properties, as derived from the image, to a table. From the material absorptivity and conductivity it can be concluded whether the material is metal, sand, grass, water, etc. However, this is not recognition because it is not yet known if a metallic object is a car or a truck, for example. For this we need to do some matching based on the shape of the objects. One way of matching shape is by template matching or generalized correlation. The absorptivity and conductivity images can be correlated with templates of absorptivity and conductivity of objects. The template with the highest correlation value wins and is the recognized object. Unfortunately this method will not work well when the object is partially occluded by clutter in the image.

A system for identifying physical objects from infrared images of said objects of the present invention comprises circuitry for deriving a heat balance equation of the objects, circuitry for generating indices of the objects pertaining to the infrared absorptivity and conductivity of the objects from the derived heat balance equation, and circuitry for comparing individual index regions of the generated indices with similar individual regions of the prestored indices. Alternatively, a method of identifying physical objects from infrared images of said objects of the present invention comprises the steps of deriving a heat balance equation of the objects, generating indices of the objects pertaining to the infrared absorptivity and conductivity of the objects from the derived heat balance equation, and comparing individual index regions of the generated indices with similar individual regions of the prestored indices.

To accomplish recognition in the context of partial object occlusion, an approach based on more locally computed and robust shape cues must be used. For example, corners and curves in the object boundary can be used for model-based matching. In this scheme, boundaries of the object are extracted from the absorptivity and conductivity images. (Note, the boundaries can be extracted more *reliably* here than in the original infrared image because absorptivity and conductivity are more invariant than intensity values in infrared images. For example, absorptivity and conductivity do not change with respect to time of day, the incident solar radiation, etc., and are the same for the hot and cold parts of a material.) Boundaries of the object can be extracted by using standard edge detection schemes, for example, the canny edge detector described in J. Canny's paper "A Computational Approach to Edge Detection," published in *IEEE Transactions on Pattern Analysis and Machine Intelligence*, PAMI-8(6):679-698, Nov. 1986. (The edges in the boundary are expected to be step edges because of the difference between the absorptivity and conductivity of the object with respect to that of the background.) The complementary approach is extracting the boundaries by region segmentation. Corners are found in the boundaries and curves are fit.

A system for identifying physical objects from infrared images of the objects of the present invention comprises circuitry for deriving a heat balance equation of the objects, circuitry for generating indices of the objects pertaining to the infrared absorptivity and conductivity of the objects from the derived heat balance equation, the indices arranged in regions, circuitry for detecting curves and corners from the regions of the indices, and circuitry for matching detected curves and corners of regions of the generated indices with curves and corners of regions of prestored indices. Alternatively, a method of identifying physical objects from infrared images of the objects of the present invention comprises the steps of deriving a heat balance equation of the objects, generating indices of the objects pertaining to the infrared absorptivity and conductivity of the objects from the derived heat balance equation, the indices arranged in regions, detecting curves and corners from the regions of the indices, and matching detected curves and corners of regions of the generated indices with curves and corners of regions of the prestored indices.

Figure 6:
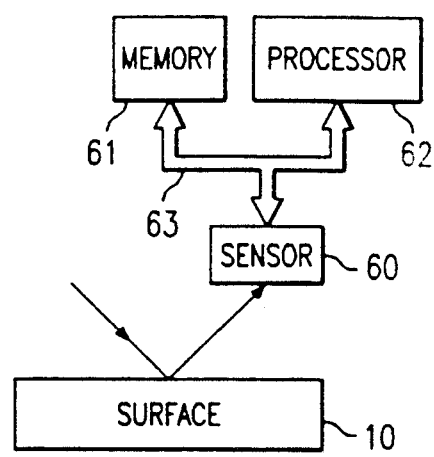
FIG. 6 shows one illustrative example of a system using the inventive concepts.

FIG. 6 shows a system where infrared energy rays 601 impact surface 10. The absorption and conduction of these rays by surface 10 is calculated in the manner previously described and stored in a memory 61. Sensor 60 receives the image which is presented to processor 62 and memory 61 via bus 63 to determine a proper match. In this example, the absorptivity and conductivity of the received infrared image would be derived as discussed above using processor 62 and comparison with prestored models in memory 61 would be made.

Note that the preferred embodiment of the present invention does not depend on the type of surface being studied. Thus, the present invention has application across all sorts of sensor data surfaces and can be used for any surface or terrain. Also note that the embodiment shows a processor and memory for performing the various functions, but a specific circuit could be designed by those skilled in the art to perform one or all of the steps of the method.

An additional use of absorptivity and conductivity values computed from infrared imagery is discussed here. These values are computed from an image, of say a particular region of interest, acquired at a particular time of day or night. They can then be used to simulate an image of the same region at any other specified time of day or night. This is done by substituting the computed absorptivity and conductivity values in the heat balance equation (equation (6)) for various values of f(t), the time dependent term representing the temporal variation in the image content. The ambient temperature term in the same equation can be varied to simulate different levels of ambient temperature (for say summer and winter days). Such image simulation is useful in training programs in the operation and image interpretation of infrared imaging systems.

Although this description describes the invention with reference to the above specified embodiments, the claims and not this description limit the scope of the invention. Various modifications of the disclosed embodiment, as well as alternative embodiments of the invention, will become apparent to persons skilled in the art upon reference to the above description. Therefore, the appended claims will cover such modifications that fall within the true scope of the invention.

What is claimed is:

1. The method of generating indices of a surface for storage in a data base, said method comprising the steps of:
   receiving a single image of a surface;
   generating a heat balance equation of said surface from said single image;
   solving said equation from said single image to obtain the heat absorptivity and conductivity of said surface; and
   establishing indices of said surface for storage in a data base based on the heat absorptivity and conductivity obtained from said step of solving.

2. The method set forth in claim 1 further comprising the steps of:
   obtaining a single new image of a surface;
   generating a heat balance equation of said surface from said single new image;
   solving said new image equation to obtain heat absorptivity and conductivity of said new image to establish indices of said new image;
   comparing said new image indices to indices stored in said data base; and
   generating a probable match between previous stored surface indices and said indices of said new image.

3. The method set forth in claim 2 wherein the indices for a given surface area, whether stored in said data base or generated from said new image, are broken into regions, and wherein the method further includes the step of:
   comparing individual index regions of a new surface against similar individual stored index regions.

4. The method set forth in claim 3 wherein said index regions contain curves and corners, and wherein the method further includes the step of:
   detecting the curves and corners of the index regions of said new image; and
   matching said detected curves and corners against curves and corners of said stored index regions.

5. The method set forth in claim 1 wherein said single image is obtained at a first point in time, said method further comprising the step of:
   generating from said established indices for a surface synthetic images of said surface representing said surface at a second point in time.

6. A circuit for generating indices of a surface for storage in a data base, said circuit comprising:
   circuitry for receiving an image of a surface;
   circuitry for generating a heat balance equation of said surface from said single image;
   circuitry for solving said equation from said single image to obtain the heat absorptivity and conductivity of said surface; and
   circuitry for establishing indices of said surface for storage in a data base based on the heat absorptivity and conductivity obtained from said circuitry for solving.

7. The method set forth in claim 6 further comprising the steps of:
   circuitry for obtaining a single new image of a surface;
   circuitry for generating a heat balance equation of said surface from said single new image;
   circuitry for solving said new image equation to obtain heat absorptivity and conductivity of said new image to establish indices of said new image;
   circuitry for comparing said new image indices to indices stored in said data base; and
   circuitry for generating a probable match between previous stored surface indices and said indices of said new image.

8. The method set forth in claim 7 wherein the indices for a given surface area, whether stored in said data base or generated from said new image, are broken into regions, and wherein the method further includes the step of:
   circuitry for comparing individual index regions of a new surface against similar individual stored index regions.

9. The method set forth in claim 8 wherein said index regions contain curves and corners, and wherein the method further includes the step of:
   circuitry for detecting the curves and corners of the index regions of said new image; and circuitry for matching said detected curves and corners against curves and corners of said stored index regions.

10. The circuit set forth in claim 6 wherein said single image is obtained at a first point in time, said circuit further comprising:
circuitry for generating from said established indices for a surface synthetic image of said surface representing said surface at a second point in time.

11. A system for identifying physical objects from infrared images of said objects, said system comprising:
circuitry for receiving infrared images of physical objects;
circuitry for deriving a heat balance equation from said infrared images of said objects;
circuitry for generating indices of said objects pertaining to the infrared absorptivity and conductivity of said objects from said derived heat balance equation; and
circuitry for comparing said generated indices with prestored indices to thereby identify said physical objects.

12. The system set forth in claim 11 wherein said prestored indices are indicative of the infrared absorptivity and conductivity of said objects.

13. The system set forth in claim 11 wherein said system further includes:
circuitry for generating alternate images of an object from the known absorptivity and conductivity indices of said object, where the alternate image represents said object at a different point in time.

14. A system for identifying physical objects from infrared images of said objects, said system comprising:
circuitry for receiving infrared images of physical objects;
circuitry for deriving a heat balance equation from said infrared images of said objects;
circuitry for generating indices of said objects pertaining to the infrared absorptivity and conductivity of said objects from said derived heat balance equation; and
circuitry for comparing individual index regions of said generated indices with similar individual regions of said prestored indices to thereby identify said physical objects.

15. The system set forth in claim 14 wherein said prestored indices are indicative of the infrared absorptivity and conductivity of said objects.

16. A system for identifying physical objects from infrared images of said objects, said system comprising:
circuitry for receiving infrared images of physical objects;
circuitry for deriving a heat balance equation from said infrared images of said objects;
circuitry for generating indices of said objects pertaining to the infrared absorptivity and conductivity of said objects from said derived heat balance equation, said indices arranged in regions;
circuitry for detecting curves and corners from said regions of said indices; and
circuitry for matching detected curves and corners of regions of said generated indices with curves and corners of regions of said prestored indices to thereby identify said physical objects.

17. The system set forth in claim 16 wherein said prestored indices are indicative of the infrared absorptivity and conductivity of said objects.

18. A method of identifying physical objects from infrared images of said objects, said method comprising the steps of:
receiving infrared images of physical objects;
deriving a heat balance equation from said infrared images of said objects;
generating indices of said objects pertaining to the infrared absorptivity and conductivity of said objects from said derived heat balance equation; and
comparing said generated indices with prestored indices to thereby identify said physical objects.

19. The method set forth in claim 18 wherein said prestored indices are indicative of the infrared absorptivity and conductivity of said objects.

20. The method set forth in claim 18 further comprising the step of:
generating alternate images of an object from the known absorptivity and conductivity indices of said object, where the alternate image represents said object at a different point in time.

21. A method of identifying physical objects from infrared images of said objects, said method comprising the steps of:
receiving infrared images of physical objects;
deriving a heat balance equation from said infrared images of said objects;
generating indices of said objects pertaining to the infrared absorptivity and conductivity of said objects from said derived heat balance equation; and
comparing individual index regions of said generated indices with similar individual regions of said prestored indices to thereby identify said physical objects.

22. The method set forth in claim 21 wherein said prestored indices are indicative of the infrared absorptivity and conductivity of said objects.

23. A method of identifying physical objects from infrared images of said objects, said method comprising the steps of:
receiving infrared images of physical objects;
deriving a heat balance equation from said infrared images of said objects;
generating indices of said objects pertaining to the infrared absorptivity and conductivity of said objects from said derived heat balance equation, said indices arranged in regions;
detecting curves and corners from said regions of said indices; and
matching detected curves and corners of regions of said generated indices with curves and corners of regions of said prestored indices to thereby identify said physical objects.

24. The method set forth in claim 23 wherein said prestored indices are indicative of the infrared absorptivity and conductivity of said objects.

* * * * *